United States Patent [19]
Schwarz et al.

[11] Patent Number: 5,026,650
[45] Date of Patent: Jun. 25, 1991

[54] HORIZONTALLY ROTATED CELL CULTURE SYSTEM WITH A COAXIAL TUBULAR OXYGENATOR

[75] Inventors: Ray P. Schwarz, League City; David A. Wolf; Tinh T. Trinh, both of Houston, all of Tex.

[73] Assignee: The United States of Amercia as represented by the Administrator of the National Aeronautics and Space Administration, Washington, D.C.

[21] Appl. No.: 213,558

[22] Filed: Jun. 30, 1988

[51] Int. Cl.$^5$ .............................................. C12M 3/02
[52] U.S. Cl. .................................. 435/286; 435/285; 435/312; 435/313; 435/818; 261/83
[58] Field of Search ............... 435/284, 285, 286, 296, 435/312, 313, 240.25, 818, 1; 261/83, 87, 92, DIG. 28

[56] References Cited

U.S. PATENT DOCUMENTS

| | | | |
|---|---|---|---|
| 3,264,739 | 4/1981 | Grabner et al. | 435/241 |
| 3,540,700 | 11/1970 | Freedman | 435/312 X |
| 3,676,074 | 7/1972 | Shibayama et al. | 23/259.1 |
| 3,769,176 | 10/1973 | Hise et al. | 435/313 X |
| 3,812,016 | 5/1974 | Müller | 435/285 |
| 3,911,619 | 10/1975 | Dedolph | 435/285 X |
| 3,925,165 | 12/1975 | Müller | 435/285 |
| 4,208,483 | 6/1980 | Lee | 435/284 |
| 4,310,630 | 1/1982 | Girard et al. | 435/284 |
| 4,343,904 | 8/1982 | Birch et al. | 435/240 |
| 4,373,029 | 2/1983 | Nees | 435/286 |
| 4,377,639 | 3/1983 | Lee | 435/288 X |
| 4,537,860 | 8/1985 | Tolbert et al. | 435/240 |
| 4,605,626 | 8/1986 | Beck | 435/291 |
| 4,649,117 | 3/1987 | Familletti | 435/313 |
| 4,720,462 | 1/1988 | Rosenson | 435/285 |
| 4,749,654 | 6/1988 | Karrer et al. | 435/240.25 X |

FOREIGN PATENT DOCUMENTS

| | | | |
|---|---|---|---|
| 0112154 | 6/1984 | European Pat. Off. | 435/286 |
| 0164888 | 12/1985 | European Pat. Off. | 435/286 |

OTHER PUBLICATIONS

M. L. Lewis et al., "Growth and Maintenance of Anchorage Dependent Cells in Zero Headspace Bioreactor Systems Designed for Microgravity", Spacebound '87 Proceedings, Ottawa, Canada, Sep. 14, 1987.

"The Large-Scale Cultivation of Mammalian Cells", Scientific American, Jan. 1983, vol. 248, #1, pp. 36–43, authors—Joseph Feder and William R. Tolbert.

"The Clinostat—A Tool for Analysing the Influence of Acceleration on Solid—Liquid Systems", Institute for Aerospace Medicine, Cologne, Germany, Proceeding of a Workshop on Space Biology, Cologne, Germany, Mar. 9–11, 1983, pp. 97–101, author—W. Briegleb.

"Particle Orbits in a Rotating Liquid", Space Science Laboratory, NASA Marshall Space Flight Center, Huntsville, Ala. 35812, and Gyln O. Roberts, Roberts Associates, Inc., Vienna, Va. 222180, authors—William W. Fowlis & Dale M. Kornfeld.

"Gravisensitivity of the Acellular Slime Mold Physarum Polycephalum Demonstrate on the East-Rotating Clinostat", European Journal of Cell Biology, pp. 44–50, Dec. 30, 1985, authors—Ingrid Block and Wolfgang Briegleb.

*Primary Examiner*—David L. Lacey
*Assistant Examiner*—William H. Beisner
*Attorney, Agent, or Firm*—Russell E. Schlorff; Harold W. Adams; Edward K. Fein

[57] ABSTRACT

A bio-reactor system where cell growth microcarrier beads are suspended in a zero head space fluid medium by rotation about a horizontal axis and where the fluid is continuously oxygenated from a tubular membrane which rotates on a shaft together with rotation of the culture vessel. The oxygen is continuously throughput through the membrane and disbursed into the fluid medium along the length of the membrane.

8 Claims, 2 Drawing Sheets

HORIZONTALLY ROTATED CELL CULTURE SYSTEM WITH A COAXIAL TUBULAR OXYGENATOR

ORIGIN OF THE INVENTION

The invention described herein was made in the performance of work under a NASA contract and is subject to provisions of Section 305 of the National Aeronautics and Space Act of 1958, Public Law 85-568 (72 Stat. 435, 42 U.S.C. 2457).

FIELD OF THE INVENTION

The present invention relates to an improved bioreactor vessel system useful for carrying out cell and tissue culture.

BACKGROUND OF THE INVENTION

Bacterial cell culture processes have been developed for the growth of single cell bacteria, yeast and molds which can be characterized as encased with a tough cell wall. Mammalian cell culture, however, is much more complex because such cells are more delicate and have a more complex nutrient requirement for development. Large scale culture of bacterial type cells is highly developed and such culture techniques are less demanding and are not as difficult to cultivate as mammalian cells. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, mammalian cells can have a special requirement because most animal cells must attach themselves to some surface in order to duplicate. On a small scale, mammalian cells have been grown in containers with small wells or pores to provide surface anchors for the cells. However, the cell culture for mammalian cells in a container with microwells generally does not provide sufficient surface area to grow mammalian cells on a large scale basis. Also horizontal roller bottles which are partially filled with nutrient media and in which cells either attach or distributed through the media are used for cell culture. However they are inefficient from a volume perspective and induce shear inhibiting three dimensional growth of delicate tissue. To provide greater surface areas, microcarrier beads have been developed for providing surface areas for the cultured cells to attach. However, microcarrier beads with attached culture cells require means for suspension in a bio-reactor vessel to provide suspension of the cells and fresh nutrients. To obtain suspension, such bio-reactor vessels have used internal propellers or movable mechanical agitation devices which are motor driven so that the moving parts within a vessel cause agitation in the fluid medium for the suspension of mammalian cells carried on microcarrier beads.

Small bio-reactor vessels with internal moving parts may damage mammalian cells and also subject the cells to high fluid shearing stresses. If the microcarrier beads collide with one other in the suspension, the attached culture cells can be damaged.

In summary, bio-reactors used to culture mammalian cells typically utilize mechanical parts, air or fluid movement as a lift mechanism to achieve particle suspension. Such mechanisms induce damage to growing cells or tissues either directly or indirectly by fluid shear.

PRIOR ART

Prior art which is known to applicant include the following:

Paper entitled, "The Clinostat—A Tool For Analyzing The Influence Of Acceleration On Solid-Liquid Systems" by W. Briegleb, published by the proceedings of a workshop on Space Biology, Cologne Germany, on Mar. 11, 1983 (ESASP-206, May 1983). In this paper, clinostat principals are described and analyzed relative to gravity affects. Some clinostat experiments are described including experiments where cultures are grown within cylinders which are rotated about a horizontal axis.

Paper entitled, "Particle Orbits In A Rotating Liquid", by William W. Fowlis and Dale M. Kornfeld, a Nasa white paper planned for publication. The Nasa paper discloses use of latex microspheres up to 3 micrometers in diameter in a rotating reactor cylinder where the cylinder is rotated about a horizontal axis to keep the particles in suspension. The rotation of the reactor cylinder maintains the particles in suspension without agitation to cause particle collision which would result in flocculation.

U.S. Pat. No. 3,676,074 relates to an apparatus for treating organic waste where a cylinder is rotated about a stationary horizontal pipe which has a central air input for supplying an air input to the waste material.

U.S Pat. No. 4,537,860 which relates to a static or stationary system for cell culture of animal cells where the cells in the vessel are supplied with a nutrient 21 which passes through a porous tube 19 into the matrix (with cells) and that exits through passages 24 and 25. Oxygen is passed through a permeable membrane 25.

U.S. Pat. No. 4,310,630 relates to a stationary or static cell culture growth device. In the '630 patent, the patentee proposes to have a rotating cylinder about a horizontal axis which is rotatable between 5 and 20 RPM. Included within the vessel is a matrix of tubular elements 11 for providing increased surface area for growth of cells. Not all of the elements 11 are covered with nutrient and the gas is supplied through one inlet and exited through an outlet.

In U.S. Pat. No. 4,605,626, an electrode assembly 16 is rotated about a vertical axis and inert gas is passed through a gas sparger 26 for dispersal as bubbles into a bacteria solution 14. The shaft rotates and agitates while the chamber remains static.

U.S. Pat. No. 4,264,739 relates to a sparger for a mass cell culture system which is comprised of an elongated tube having a plurality of ports.

U.S. Pat. No. 4,343,904 relates to growth of animal cells and a vertical cylindrical vessel having spaced apart plates on an axial shaft. An external pumping loop is provided for circulating the contents of the vessel from the bottom to the top of the vessel. Cell growth is carried out by substantially filling the vessel with cells and growth medium and allowing the cells to settle onto disk surfaces and rotating the shaft while circulating the vessel contents from the bottom to the top for mixing.

U.S. Pat. No. 4,649,117 discloses an air lift bioreactor for maintaining cells in suspension and includes a centrally located gas inlet means at the lower end of the mixing chamber, a conical side wall in the growth chamber and introducing an oxygen containing gas to bubble up through the cells and liquid medium to carry the cells and liquid medium upward from the mixing chamber to the growth chamber and so that the cells and liquid medium flow downwardly along the conical side wall to replace the cells and liquid medium being carried upwards in the mixing chamber. The system is for agitating the cells while minimizing shear forces.

A paper entitled, "The Large Scale Cultivation of Mammalian Cells", by Joseph Feder and William R. Tolbert, published in the Scientific American Magazine, January 1983, Vol. 248, No. 1. pps. 36–43. In this paper, agitation of the cells is described as required to keep the cells suspended in the medium and describes a turbine agitator, a marine propeller agitator, and a vibro mixer for mixing. The paper also describes a perfusion reactor in which an agitation is provided by four slowly rotating flexible sheets of monofilament nylon which are rotated about a vertical axis while the medium in the main vessel is continuously pumped to the satellite filter vessel. The filter retains the cells which are pumped along with the remainder medium back into the vessel for further proliferation.

A paper entitled, "Gravinsensitivity Of The Acellular, Slime, Mold, Physarum, Polycephalum Demonstrated On The Fast Rotating Clinostat", by Ingrid Block and Wolfgang Brigleb, published in the European Journal of Cell Biology 41, pps. 44–50, 1986. This paper describes rotation of a culture vessel about a horizontal axis for the stimulation of weightlessness. The paper is a study relative to the gravity influences in the control systems of cells.

SUMMARY OF THE PRESENT INVENTION

In the present invention, a horizontally disposed cylinder with end caps defines a cell culture vessel which is rotatable about an approximate horizontal axis. One of the end caps is attached to a motor drive for rotating the cylinder about its centerline horizontal axis. A centrally located, coaxial, internal cylindrical support shaft is attached to the end caps and supports an annular tube of gas permeable membrane. In one of the end caps is an access passageway to access an oxygen containing gas through the shaft to the interior of the annular membrane at one end of the membrane. At the other end cap is an exit passageway to exit the gas through the shaft from the interior of the membrane at the other end of the membrane. The exit end cap also has separate controlled access entry ports to the interior of the cell culture vessel for sampling, changing or adding fluid or cells.

For processing of mammalian cells, the system is sterilized and fresh fluid medium, microcarrier beads, and cells are admitted to completely fill the cell culture vessel. An oxygen containing gas is admitted to the interior of the permeable membrane which prevents air bubbles from being introduced into the medium. The cylinder is rotated at a low speed within an incubator so that the circular motion of the fluid medium uniformly suspends the microbeads throughout the cylinder during the cell growth period.

The system thus involves rotating a fluid nutrient medium having zero head space having a first density about a nearly rotational horizontal axis where discrete suspension materials disposed in the fluid medium have a same or different density from the density of the fluid nutrient medium. The rotation of the fluid nutrient medium is controlled to place the discrete suspension materials in suspension at spatial locations in the fluid nutrient medium out of an interference relationship with one another by virtue of the rotation and so that they are not subjected to fluid shear forces generated by velocity gradients at the boundary layer at the vessel wall. While rotating the fluid nutrient a medium gas is allowed to exchange across a diffusion membrane to the fluid nutrient medium.

The unique design of this cell and tissue culture device was initially driven by two requirements imposed by its intended use for feasibility studies for three dimensional culture of living cells and tissues in space by NASA. These were 1) compatibility with microgravity and 2) simulation of microgravity in one G. The vessels are designed to approximate the extremely quiescent low shear environment obtainable in space where it would be unnecessary for a lifting mechanism to oppose particle sedimentation. Thus gentle culture environment was hypothesized to allow cells to achieve and maintain a three dimensional orientation, according to cellular derived forces, and thus form higher order tissue structures. The rotating wall culture vessels, with associated features herein disclosed, developed for these purposes were found to allow living cell cultures which exhibited the hypothesized features. It is observed that the rotating fluid effectively counters sedimentation and that the rotating wall effectively reduces adverse fluid velocity gradients through the boundary layer at the vessel wall. The combined effects allowed bulk cultures to be maintained with three dimensional orientations free of disruptive shear forces which would limit the viability of delicate cell types (particularly mammalian) and would limit the assembly of cells into higher order structures. It is observed in the case of attachment dependent cultures maintained on microcarrier beads that the hundreds or thousands of beads participate in the formation of large high order structures bound by cell bridging. Along the center axis of the vessel, exchange device to support cell respiration. Gas mixtures are exchanged with the external environment across a diffusion membrane attached to a cylindrical support. It was apparent to scientists utilizing this instrumentation that it offered significant advantages for earth based cell and tissue culture in terms of efficient utilization of vessel volume, logistics, and unique culture capabilities (particularly for attachment dependent microcarrier cultures). Additional benefit is derived from the efficient utilization of the vessel volume for culture allowing improved logistics where cell or cell product production is concerned.

DESCRIPTION OF THE PREFERRED EMBODIMENT

Figure 1:
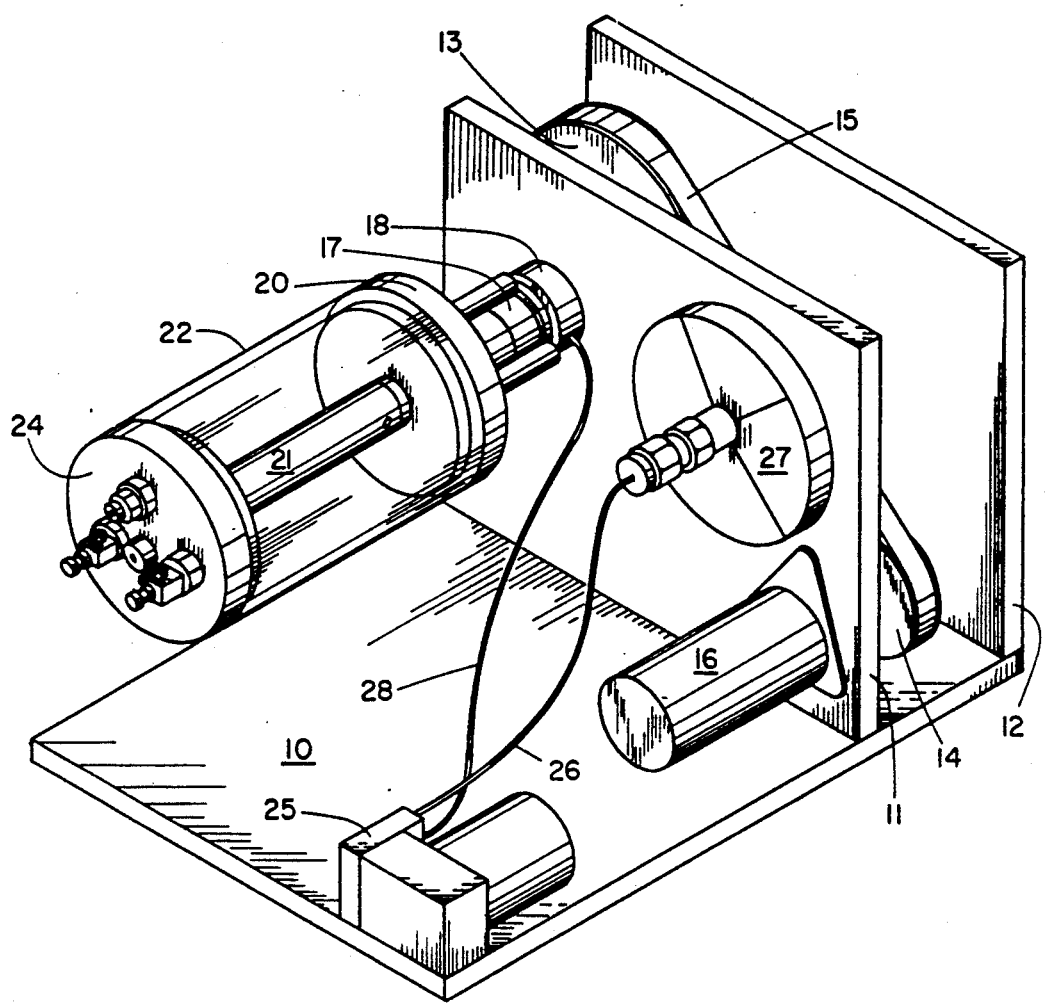
FIG. 1 shows a perspective view of the general organization of the present invention.

Referring now to FIG. 1, the general organization of the present invention is illustrated. A frame means 10 has vertical and spaced apart plates 11, 12 which support a motor pulley 14 and a housing pulley 13 where the pulleys 13, 14 are connected by a belt drive 15. The motor pulley 14 is coupled to a motor 16 which can be controlled in a well known manner to provide a desired drive speed.

The housing pulley 13 is connected to a drive shaft 17 which extends through a rotative coupling 18 to an inlet end cap 20. The inlet end cap 20 is attached to a central assembly 21 and to a tubular outer culture cylinder 22. At the other end of the central assembly 21 and the culture cylinder 22 is an outlet end cap 24.

An air pump 25 on the frame means 10 is connected by input tubing 26 to a filter 27. An output tubing 28 from the pump 25 couples to the rotative coupling 18 where the air input is coupled from a stationary annular collar to an internal passageway in the rotating drive shaft 17.

Figure 2:
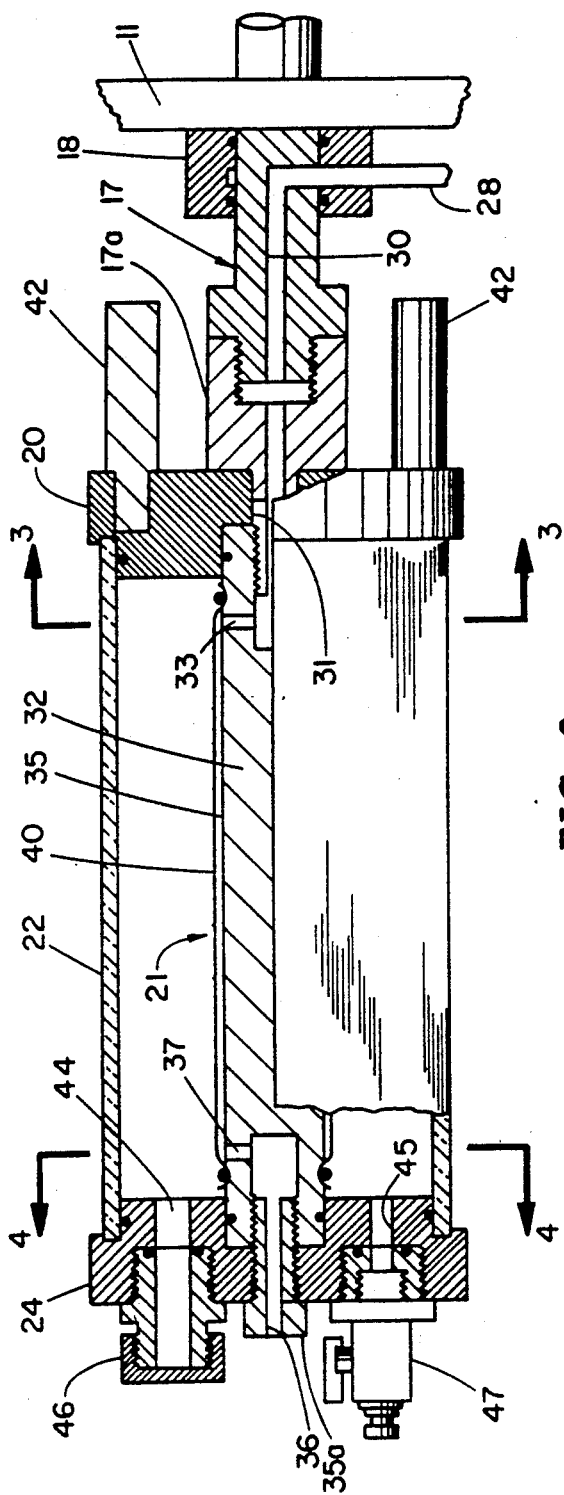
FIG. 2 shows a view in partial cross section through a horizontally rotated cell culture vessel illustrating an application of the present invention.
Figure 4:
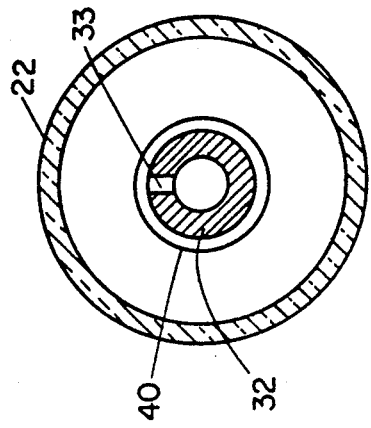
FIG. 4 is a view in cross section taken along line 4—4 of FIG. 2.
Figure 3:
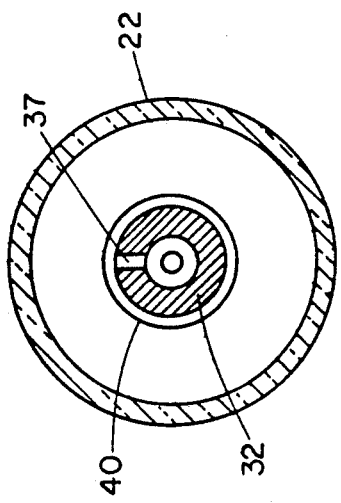
FIG. 3 is a view in cross section taken along line 3—3 of FIG. 2.

Referring now to FIG. 2, the cell culture system of the present invention is illustrated in partial cross section where the rotative coupling 18 receives the output tubing 28 and the drive shaft 17 has a central air inlet passageway 30 for the passage of air. The drive shaft 17 is attached to a coupling shaft 17a which extends through a central opening 31 in the inlet end cap 20. The coupling shaft 17a is threadedly attached to a cylindrically shaped, central support member 32. The central passageway 30 extends inwardly through the shafts 17, 17a to a transverse opening 33 which couples the air inlet passageway 30 to the exterior surface 35 of the central support member 32. The central support member 32 is sealingly received in a counterbore in the inlet end cap 20 and at its opposite end, the support member 32 is sealingly received in a counterbore of the outlet end cap 24. A tubular outlet member 35a is threadedly attached through a bore in the outlet end cap 24 to a blind bore in the support member 32 and an air exit passageway 36 in the outlet coupling is connected by a transverse opening 37 to the exterior surface 35 of the central support member 32. A tubular oxygen permeable membrane 40 is disposed over the central support member 32 and has its ends extending over the openings 33 and 37 in the central support member 32 so that the membrane 40 can be sealingly attached to the central support member 32 by 0-rings or the like. Thus an air passageway is provided for an input of air through the passageway 30 and the transverse opening 33, through the annular space between the inner wall of the membrane 40 and the outer wall of the central support member 32 to the exit transverse opening 37 and to the exit passageway 36. The membrane 40 may be made of silicone rubber which operates under air pressure to permit oxygen to permeate through the wall of the membrane into the annulus of fluid medium surrounding the membrane and carbon dioxide to diffuse in the opposite direction.

Coaxially disposed about the central support shaft 32 is a tubular outer cylinder 22 which can be glass. The cylinder 22 is sealing received on the end caps 20, 24 and defines an annular culture chamber between the inner wall of the cylinder 22 and the outer surface of the membrane 40. On the inlet end cap 20 are circumferentially spaced apart cylindrical members 42. When the coupling shaft 17a is detached from the shaft 17, the members 42 provide a base for standing the cylinder 22 upright or in a vertical position for sampling, changing or adding fluids to the system.

In the outlet end cap 24, there are two or more access ports 44, 45 each having closure means 46. A hypodermic needle with fluid medium can be inserted through one access port to inject fluid when withdrawing fluid from the other port. In this regard samples or media can be withdrawn without forming an air space, thereby preserving the zero head space.

The present invention thus involves the central cylindrical core which is a source of oxygenation through the cylindrical membrane and the membrane and outer wall of the vessel are rotated about a horizontal axis. This involves a type of clinostat principal, i.e. a principal that fluid rotated about a horizontal or nearly horizontal axis can effectively suspend particles in the fluid independent of the effects of gravity. The rotational speed of the cylinder 22 effectively eliminates the velocity gradient at the boundary layer between the fluid and the cylinder wall. Thus, shear effects caused with a rotating fluid and stationary wall are significantly reduced or eliminated.

In an experimental use a high density culture of baby hamster kidney cells were produced by utilizing beads constructed from cytodex 3 material and utilizing a microcarrier medium prepared with low bicarbonate and 20 mM HEPES buffer, 10% fetal calf serum and antibiotics (PH 7.35+10 ml/1 NaOH (ln) where the seeding density of the cells were 6 to 8 cells per bead and the bead density was 15 mg/ml.

In the process the vessel was soaked in ethyl alcohol overnight, rinsed with Millipore quality water, wrapped and autoclaved. After cooling, the vessel was rinsed with complete medium prior to loading the beads. The beads were loaded into the vessel via the syringe barrel attached to one of the ports and the vessel was filled with medium and placed in an incubator and allowed to run for about 30 minutes to equilibrate while preparing the cells. The stored frozen cells were thawed, suspended in the medium, counted, diluted and loaded into the vessel via a syringe attached to one of the ports. The vessel was subsequently filled with culture grown medium and rotation rate was set at 10 rpm. The air pump was actuated to move incubator air across the exchange membrane. Samples were withdrawn for cell counts at 1, 3 and 5 hours and approximately 24 hours thereafter.

The results of the tests were that the cells attach and grow on the beads at the high density of 15 mg/ml. The total cell counts at maximum cell number showed about $1.1 \times 10^9$ cells at 168 hours. The attachment of cells to the beads occurred normally within the first hour. Fluid media change was made every 48 hours.

Cell growth cultures have been successfully produced by use of the present invention in development of human colon carcinoma cells, human embryonic kidney cells, tobacco callus cells, normal human embryonic kerotinocytes cells, normal human colon fibroblast cells, human promyleocytic leukemia cells, bovine embryonic kidney cells, normal embryonic lung cells, mouse melanoma cells, mouse hybridoma cells. As can be appreciated, the ability to grow mammalian cell cultures in a controlled environment is significant.

The clinostatic principle involved is that a fluid rotating (at the appropriate rate) about a horizontal or nearly horizontal axis (with respect to gravity) allows cells or cell attachment substrates having a density different from the fluid to travel in a nearly circular path and to deviate insignificantly from the fluid path. From the rotating reference frame the gravity vector is observed to rotate so that its time average is nearly zero. This allows for suspension of the particles in a carrier medium with low fluid shear and with low interference. The vessel wall is rotated in order to reduce the adverse fluid velocity gradient through the boundary layer at this wall (which would occur at the interface between the moving fluid and fixed wall). The rotating wall is sufficient to cause fluid rotation due to viscosity. The operating limits are defined by the sedimentation rate of the particles in the fluid medium and the acceptable centrifugal force due to rotation. The present invention has excellent operating characteristics between 5 and 40 RPM for culture of anchorage dependent cells on microcarrier beads. It is possible to vary the angular rotation rate in order to induce secondary flow patterns within the vessel, at the expense of transient fluid velocity gradients at the wall boundary layers, useful for distributing nutrients or waste products.

In the present invention the cell culture vessel is a cylinder rotated about a horizontal axis and the process utilizes zero head space of fluid medium within the vessel. The entire cylindrical vessel is rotated to suspend the cells by rotation of the vessel so that suspension of the cells is such that the beads are not agitated into contact with one another. At the same time the velocity gradient at the boundary layer of the fluid and the vessel wall is minimized. As a result of the horizontal orientation and clinostatic suspension of the particles, less mixing force is required to move a particle from the bottom to the top of the vessel. The zero head space results in no air bubbles which cause disruption of fluid streamlines thus subjecting the culture to adverse shear effects. The central gas exchange membrane permits a uniform dispersal of component gases from a central core to the fluid medium and reverse to allow culture respiration.

It will be apparent to those skilled in the art that various changes may be made in the invention without departing from the spirit and scope thereof and therefore the invention is not limited by that which is enclosed in the drawings and specifications, but only as indicated in the appended claims.

We claim:

1. A bio-reactor for maintaining mammalian cells in suspension while subjecting such cells to nutrients and oxygen, said bio-reactor including
    an elongated tubular culture vessel;
    end caps enclosing the ends of said culture vessel;
    a shaft co-axially disposed in said culture vessel and extending between said end caps;
    a tubular membrane disposed over said shaft between said end caps and sealed with respect to said shaft for defining an annular passageway between said membrane and said shaft and for defining an annular culture chamber between said membrane and the inner wall of said culture vessel;
    oxygenation means for admitting an oxygen containing gas under pressure at one end of said annular passageway defined by said membrane and for exiting the gas at the other end of said annular passageway defined by said membrane, said membrane being oxygen permeable for exchange of component gases with said culture chamber;
    means for admitting a fluid culture medium microcarrier beads and cells into said culture chamber for completely filling said culture chamber and for development of cell growth on the beads; and
    means for rotating said culture vessel, said shaft and said membrane about a horizontal axis at a rate sufficient to suspend the beads in a fluid motion while admitting oxygen about the circumference of the membrane on said shaft.

2. The bio-reactor as set forth in claim 1 wherein said oxygenation means further includes a passageway in the shaft in flow communication with said annular passageway and a rotative coupling for coupling, a source of oxygen containing gas to said passageway in the shaft.

3. The bioreactor as set forth in claim 1 wherein said rotating means further comprises speed control means for increasing or decreasing the speed of rotation whereby the microcarrier beads with the cells attached are maintained in suspension at spatial locations out of an interference relationship with one another.

4. The cio-reactor as set forth in claim 1 further including first access means in one of said end caps for admitting and drawing fluid culture medium from said culture chamber.

5. The bioreactor set forth in claim 4 further including another access means in said one end cap to simultaneously inject fluid when withdrawing fluid from the first access means to prevent forming an air space in the culture vessel thereby preserving zero head space.

6. The bioreactor set forth in claim 5 wherein said shaft is connected to said rotating means and further including means for disconnecting said shaft from said rotating means, and means on the other of said end caps permitting the culture vessel to stand upright for sampling, charging or adding fluid to the culture vessel.

7. A bio-reactor for culturing anchorage dependent living cells in suspension while subjecting such cells to nutrients and oxygen, said bio-reactor including
    a tubular culture vessel;
    closure means enclosing the ends of said culture vessel;
    a shaft co-axially deposed in said culture vessel and extending between said closure means;
    a tubular membrane disposed over said shaft between said closure means and sealed with respect to said shaft for defining an annular passageway between said membrane and said shaft and for defining an annular culture chamber between said membrane and the inner wall of said culture vessel;
    oxygenation for admitting respiratory gases under pressure at one end of said annular passageway defined by said membrane and for exiting the gases at the other end of said annular passageway defined by said membrane, said membrane being permeable to said respiratory gases for exchange of component gases with said culture chamber, said oxygenation means including an input passage in the shaft with an input opening at one end of the annular passageway defined by said membrane and an output passage in the shaft with an output opening at the other end of the annular passageway defined by the membrane, said oxygenation means further including connecting means for coupling said input passage to a stationary gas supply;
    means for admitting a fluid culture medium, microcarrier beads and cells into said culture chamber for completely filling said culture chamber; and
    means for rotating said culture vessel, said shaft and said membrane about a horizontal axis at a rate sufficient to suspend the beads in the fluid medium while permitting respiratory gas exchange about the circumference of the membrane on said shaft for the development of cell growth.

8. The bio-reactor as set forth in claim 7 further including access means in said closure means for simultaneously admitting and withdrawing fluid culture medium from said culture chamber without forming an air space.

* * * * *